(12) United States Patent
Ojala et al.

(10) Patent No.: US 11,981,633 B2
(45) Date of Patent: May 14, 2024

(54) METHOD TO PRODUCE BIO-RENEWABLE PROPYLENE FROM OILS AND FATS

(71) Applicant: Neste Oyj, Espoo (FI)

(72) Inventors: Antti Ojala, Porvoo (FI); Risto Vapola, Porvoo (FI); Anna Karvo, Porvoo (FI); Rogier Van De Velde, Porvoo (FI)

(73) Assignee: NESTE OYJ, Espoo (FI)

( * ) Notice: Subject to any disclaimer, the term of this patent is extended or adjusted under 35 U.S.C. 154(b) by 114 days.

(21) Appl. No.: 17/265,257

(22) PCT Filed: Jul. 25, 2019

(86) PCT No.: PCT/EP2019/070040
§ 371 (c)(1),
(2) Date: Feb. 2, 2021

(87) PCT Pub. No.: WO2020/025441
PCT Pub. Date: Feb. 6, 2020

(65) Prior Publication Data
US 2021/0300843 A1 Sep. 30, 2021

(30) Foreign Application Priority Data
Aug. 3, 2018 (FI) ..................... 20185671

(51) Int. Cl.
C07C 5/32 (2006.01)
C07C 1/207 (2006.01)
(Continued)

(52) U.S. Cl.
CPC .............. C07C 5/32 (2013.01); C07C 1/2078 (2013.01); C07C 1/24 (2013.01); C07C 4/02 (2013.01);
(Continued)

(58) Field of Classification Search
CPC ........... C07C 5/32; C07C 1/2078; C07C 1/24; C07C 4/02; C07C 5/22; C07C 7/144;
(Continued)

(56) References Cited

U.S. PATENT DOCUMENTS 3,665,049 A * 5/1972 Cornelius ................ B01J 23/26
502/320
3,776,838 A * 12/1973 Youngblood et al. . C10G 11/18
208/77
(Continued)

FOREIGN PATENT DOCUMENTS

CN 1143068 A 2/1997
CN 101015802 A 8/2007
(Continued)

OTHER PUBLICATIONS

International Preliminary Report on Patentability (PCT/IPEA/416 and PCT/IPEA/409) dated Oct. 19, 2020, by the European Patent Office as the International Preliminary Examining Authority for International Application No. PCT/EP2019/070040.
(Continued)

Primary Examiner — Thuan D Dang
(74) Attorney, Agent, or Firm — BUCHANAN INGERSOLL & ROONEY PC

(57) ABSTRACT

A method is disclosed for upgrading a bio-based material, the method including pretreating bio-renewable oil(s) and/or fat(s) to provide a bio-renewable raw material, deoxygenating the bio-renewable raw material, followed by separation, to provide a propane feed, and subjecting the propane feed to dehydrogenation and to separation to provide a propylene material.

22 Claims, 1 Drawing Sheet

(51) Int. Cl.
| | |
|---|---|
| *C07C 1/24* | (2006.01) |
| *C07C 4/02* | (2006.01) |
| *C07C 5/22* | (2006.01) |
| *C07C 7/144* | (2006.01) |
| *C08L 23/14* | (2006.01) |

(52) U.S. Cl.
CPC ............... *C07C 5/22* (2013.01); *C07C 7/144* (2013.01); *C08L 23/14* (2013.01)

(58) Field of Classification Search
CPC . C07C 9/08; C08L 23/14; Y02P 30/20; C10G 11/00; C10G 51/00; C10G 57/02; C10G 2400/20; C10G 50/00; C10G 3/50; C10G 3/00
See application file for complete search history.

(56) References Cited

U.S. PATENT DOCUMENTS

| | | | |
|---|---|---|---|
| 5,705,684 | A | 1/1998 | Hefner et al. |
| 2009/0250376 | A1 | 10/2009 | Brandvold et al. |
| 2010/0043279 | A1 | 2/2010 | Abhari et al. |
| 2011/0230632 | A1 | 9/2011 | Abhari |
| 2012/0157728 | A1 | 6/2012 | Vermeiren et al. |
| 2013/0296497 | A1* | 11/2013 | Jeong ................... C08F 297/08 525/321 |
| 2014/0155665 | A1 | 6/2014 | Vermeiren et al. |
| 2015/0141715 | A1 | 5/2015 | Vermeiren et al. |
| 2015/0210932 | A1 | 7/2015 | Fingland et al. |
| 2016/0046873 | A1 | 2/2016 | Räsänen et al. |
| 2017/0081262 | A1* | 3/2017 | Savolainen ............. C10L 3/101 |
| 2018/0216010 | A1* | 8/2018 | Hong ....................... C10G 7/00 |

FOREIGN PATENT DOCUMENTS

| | | |
|---|---|---|
| CN | 111533634 A | 8/2020 |
| EP | 1 741 768 A1 | 10/2007 |
| EP | 2130812 A1 | 12/2009 |
| EP | 2290034 A1 | 3/2011 |
| EP | 2290035 A1 | 3/2011 |
| KR | 101424897 B1 | 8/2014 |
| WO | 9527019 A1 | 10/1995 |
| WO | 2009039335 A1 | 3/2009 |
| WO | 2014079785 A2 | 5/2014 |
| WO | 2014167181 A1 | 10/2014 |

OTHER PUBLICATIONS

International Search Report (PCT/ISA/210) and Written Opinion (PCT/ISA/237) dated Oct. 25, 2019, by the European Patent Office as the International Searching Authority for International Application No. PCT/EP2019/070040.

Office Action dated Nov. 26, 2021, by the Canadian Patent Office in corresponding Canadian Patent Application No. 3,105,006. (5 pages).

First Office Action dated Feb. 16, 2022, by the Chinese Patent Office in corresponding Chinese Patent Application No. 201980047364.6, and an English Translation of the Office Action. (18 pages).

Office Action (Notice of Reasons for Refusal) dated May 17, 2022, by the Japanese Patent Office in corresponding Japanese Patent Application No. 2021-505911, and an English Translation of the Office Action. (10 pages).

Office Action (Request for the Submission of an Opinion) dated Sep. 6, 2022, by the Korean Patent Office in corresponding Korean Patent Application No. 10-2021-7002826, and an English Translation of the Office Action. (16 pages).

Second Office Action dated Nov. 18, 2022, by the Chinese Patent Office in corresponding Chinese Patent Application No. 201980047364. 6, and an English Translation of the Office Action. (19 pages).

Office Action dated Jun. 9, 2022, by the Canadian Patent Office in corresponding Canadian Patent Application No. 3,105,006. (4 pages).

Search Report and Written Opinion dated Sep. 20, 2022, by the Singaporean Patent Office in corresponding Singaporean Application No. 11202100964T. (6 pages).

Office Action dated Jun. 6, 2022, by the Chinese Patent Office in corresponding Chinese Patent Application No. 201980047364.6. (4 pages).

Efterpi S. Vasiliadou et al., "Production of Biopropylene Using Biomass-Derived Sources. In: Sustainable Inorganic. Chemistry", 1st edition, Edited by David A. Atwood, Chichester, UK: John Wiley & Sons, Oct. 2016, 129-140, ISBN 978-1-118-70342-7. (cited in Office Action dated May 5, 2023, by the Finnish Patent and Registration Office in Corresponding Finnish Patent Application No. 20185671).

Office Action dated Mar. 17, 2023, by the State Intellectual Property Office of China in corresponding Chinese Patent Application No. 201980047364.6, and a machine English translation of the Office Action. (20 pages).

Office Action dated Apr. 10, 2023, by the Brazilian Patent Office in corresponding Brazilian Patent Application No. 112021001801-8, with an English translation of Office Action (8 pages).

Office Action (Decision of Rejection) dated Jul. 29, 2023, by the Chinese Patent Office in corresponding Chinese Patent Application No. 201980047364.6, and a partial English Translation of the Office Action. (9 pages).

Office Action dated Aug. 3, 2023, by the Finnish Patent Office in corresponding Finnish Patent Application No. 20185671. (4 pages).

Office Action (Communication) issued on Apr. 25, 2022, by the European Patent Office in corresponding European Patent Application No. 19 749 626.8. (8 pages).

Office Action (Opinion on Patentability) issued on Nov. 1, 2021, by the Finnish Patent Office in corresponding Finnish Patent Application No. 20185671. (5 pages).

Office Action issued on Dec. 6, 2023, by the Brazilian Patent Office in corresponding Brazilian Patent Application No. 112021001801-8. (4 pages).

\* cited by examiner

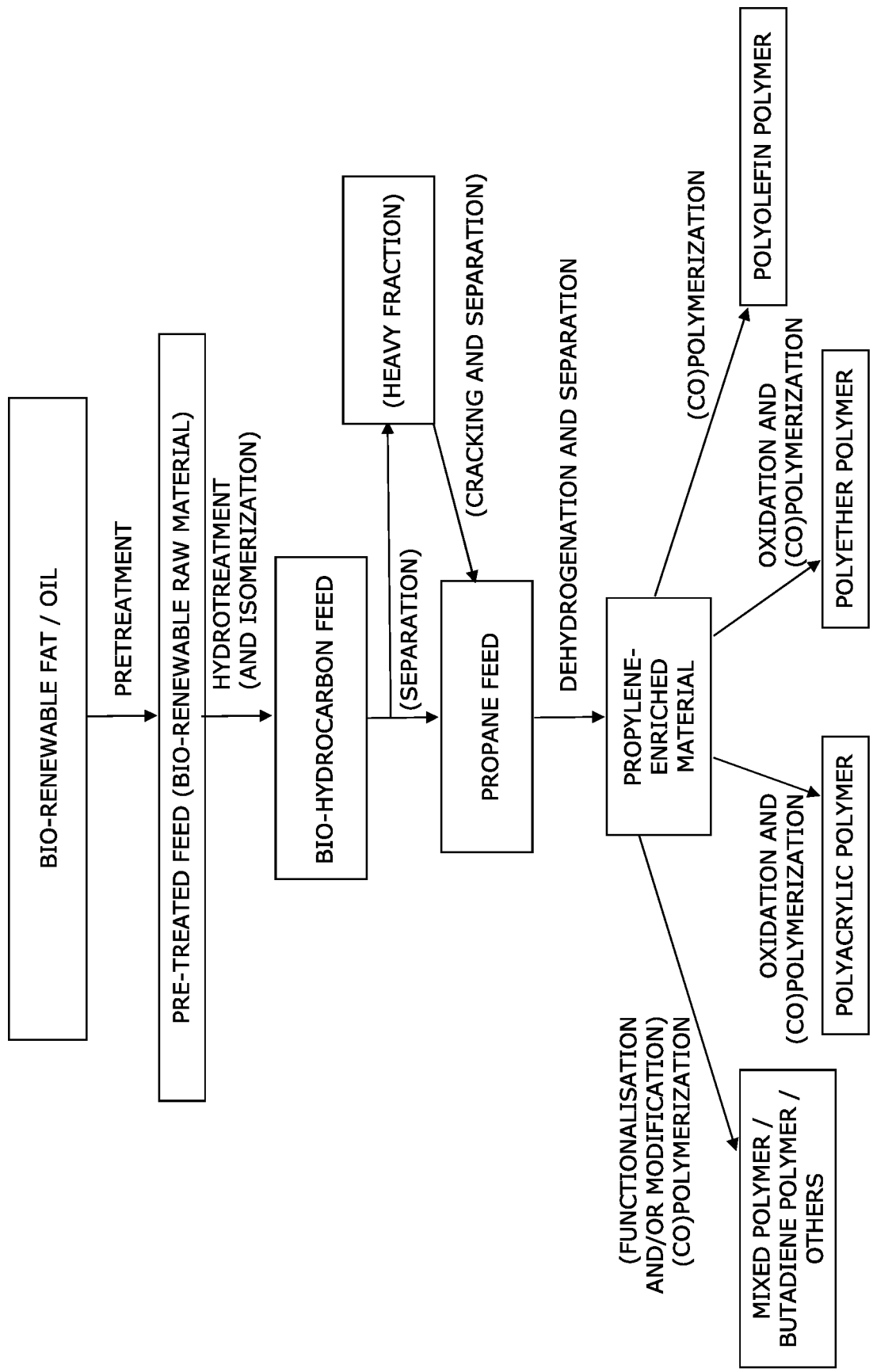

METHOD TO PRODUCE BIO-RENEWABLE PROPYLENE FROM OILS AND FATS

TECHNICAL FIELD

The present invention relates to a method for producing bio-renewable propylene (propene) from oil(s) and/or fat(s). Specifically, the present invention relates to a method of subjecting naturally occurring (renewable) oils(s) and/or fat(s) to hydrogenation, separating a propane feed from the hydrogenation product and subjecting the propane feed to dehydrogenation to provide a propylene material after purification/separation. The propylene material may then be further processed.

TECHNICAL BACKGROUND

Propylene is a base material for several high volume chemicals such as acrylic acid, propylene oxide and polypropylene that are consumed annually about 2700 kt, 9000 kt and 60 000 kt, respectively. Acrylic acids are mainly used in the production of super absorbents, coatings and paints. Propylene oxide is as precursor for several high volume chemicals such as butanediol, polyether polyol and propylene glycol. Polypropylene (PP) is the second most common thermoplastic polymer and it is found in many applications such as packages, transportation, construction, consumer goods, electronics etc.

The majority of the propylene production at present is based on fossil material and involves large scale cracking facilities.

Presently available methods to produce bio-based polypropylene, propylene oxide or acrylic acid have only limited value for industrial scale production.

WO 2014/079785 A1 discloses a method for producing water absorbent polymer particles comprising thermal cracking/steam cracking e.g. oils/fats ("bio-naphtha") to produce a mixture comprising propane and propylene, gas phase oxidation of the mixture to form acrylic acid and propionic acid, and subsequent polymerization.

EP 2 290 034 A1 discloses a method of steam-cracking free fatty acids (FFA) and/or fats/oils to produce mainly propylene and ethylene.

US 2011/0230632 A1 discloses a method for conversion of biomass to polymers, including steam cracking of hydrocarbons derived from biomass and subsequent polymerization of olefins obtained by steam cracking.

Bio-renewable oil(s) and fat(s) comprise glycerides, and every glyceride molecule (e.g. mono-, di-, triglyceridic) contains a glycerol backbone. Upon hydrogenation, this glycerol backbone is usually converted into bio-propane. This bio-propane is currently marketed as a fuel.

SUMMARY OF THE INVENTION

It is an object of the present invention to provide an improved method for the production of propylene.

The inventors of the present invention surprisingly found that propane originating from hydrogenated bio-renewable oil(s) and/or fat(s) can be used as a valuable raw material for a dehydrogenation process where it is converted to propylene. Specifically, the inventors found that propane produced according to the present invention can be used as raw material for dehydrogenation similar to fossil propane, while the bio-renewable propane feed of the present invention is favourable over fossil propane feeds in terms of its usability in the dehydrogenation process.

The present invention relates to one or more of the following items:
1. A method for upgrading a bio-based material, the method comprising the steps of
    pretreating bio-renewable oil(s) and/or fat(s) to provide a bio-renewable raw material,
    deoxygenating the bio-renewable raw material, followed by separation, to provide a propane feed, and
    subjecting the propane feed to dehydrogenation and to separation to provide a propylene material.

The method of the present invention provides the benefit that a highly pure propylene material can be produced and furthermore the dehydrogenation step is very effective because the propane feed can be provided with high purity, thus reducing catalyst poisoning. That is, other than in the case of fossil feeds (mainly comprising hydrocarbons) used for propylene production, the potential catalyst-poisoning substances (mainly S, N and P containing material) can be easily removed in the pre-treatment step because these materials can be separated from the oxygen-containing bio-renewable oil(s) and/or fat(s) using simple and effective procedures.

Moreover, since the propane feed can be produced in high purity with only few catalyst-poisoning impurities and furthermore containing only low amounts of higher-boiling hydrocarbons, a highly pure and highly concentrated propylene material can be produced which is a valuable material for further use e.g. in polymer chemistry.

2. The method according to item 1, wherein the deoxygenation step is at least selected from hydrodeoxygenation, decarboxylation, decarbonylation, and hydrocracking, preferably hydrodeoxygenation.

The deoxygenation step is most suitably conduced as a hydrodeoxygenation step, especially when the bio-renewable raw material contains glycerides and/or glycerol. That is, using this procedure, the glycerol-based structures are converted to propane with high yields.

3. The method according to item 1 or 2, comprising the step of subjecting the C3+ components produced in the deoxygenation step and separated from the propane feed to cracking, after optional isomerization, to produce more gases, followed by separation of at least propane in the gases and combining the thus obtained propane with the propane feed.

In the context of the present invention, C3+ components refer to components having more than 3 carbon atoms. Since the components are derived from the deoxygenation step, these C3+ components will usually have more than 3 carbon atoms bound to each other as a chain or as a (poly)cycle with no heteroatoms. By subjecting the C3+ components to cracking, the yield of propane can be further increased.

4. The method according to any one of the preceding items, further comprising an isomerisation step after the deoxygenation step.

5. The method according to any one of the preceding items, wherein the pretreatment step is a step of reducing contaminants containing S, N and/or P in the oil(s) and/or fat(s) to produce the bio-renewable raw material.

6. The method according to any one of the preceding items, wherein the pretreatment comprises one or more selected from washing, degumming, bleaching, distillation, fractionation, rendering, heat treatment, evaporation, filtering, adsorption, hydrodeoxygenation, centrifugation or precipitation.

The above pretreatment methods are simple and effective methods for removing the potentially catalyst-poisoning S, N and P contaminants.

7. The method according to any one of the preceding items, wherein the step of pretreatment of the bio-renewable raw material comprises at least one of partial hydrogenation, partial deoxygenation, hydrolysis and transesterification.
8. The method according to any one of the preceding items, wherein the bio-renewable raw material comprises glycerol and/or fatty acid esters.
9. The method according to item 8, wherein the bio-renewable raw material comprises glycerol which is produced by hydrolysis and/or transesterification of the bio-renewable oil(s) and/or fat(s).

Specifically, the bio-renewable raw material may be a stream containing (or essentially consisting of) glycerol produced by hydrolysis and/or transesterification of oil(s) and/or fat(s), which is a usual procedure in the production of biodiesel. For example the preparation of fatty-acid methyl ester (FAME) involves transesterification of e.g. glyceride feedstocks, and glycerol is a by-product of FAME production amounting to approximately 10 wt % of the production of FAME. Commonly, the glycerol was regarded as an impurity and/or side product of low value in these processes.

10. The method according to any one of the preceding items, wherein the propane feed has a propane content of at least 80 wt.-%, preferably at least 85 wt.-%, at least 87 wt.-%, at least 88 wt.-%, at least 89 wt.-%, at least 90 wt.-%, at least 91 wt.-%, at least 92 wt.-%, at least 93 wt.-%, at least 94 wt.-%, at least 95 wt.-%, at least 96 wt.-%, or least 97 wt.-%.
11. The method according to any one of the preceding items, wherein the bio-renewable raw material has a total sulfur content of at most 500 ppm, preferably at most 300 ppm, at most 200 ppm, at most 100 ppm, at most 60 ppm, at most 50 ppm, at most 40 ppm, at most 35 ppm, at most 30 ppm, at most 25 ppm, at most 20 ppm, at most 15 ppm, at most 10 ppm, or at most 5 ppm.
12. The method according to any one of the preceding items, wherein bio-renewable raw material has a total phosphorus content of at most 300 ppm, preferably at most 200 ppm, at most 100 ppm, at most 80 ppm, at most 50 ppm, at most 40 ppm, at most 35 ppm, at most 30 ppm, at most 25 ppm, at most 20 ppm, at most 15 ppm, at most 10 ppm, or at most 5 ppm.
13. The method according to any one of the preceding items, wherein bio-renewable raw material has a total nitrogen content of at most 400 ppm, preferably at most 300 ppm, at most 200 ppm, at most 100 ppm, at most 60 ppm, at most 40 ppm, at most 35 ppm, at most 30 ppm, at most 25 ppm, at most 20 ppm, at most 15 ppm, at most 10 ppm, or at most 5 ppm.

The contents of the above-mentioned contaminants can be reduced to considerably low amounts using comparatively simple procedures. This allows production of a propane feed having low amounts of contaminants and thus being specifically suited for being upgraded to higher-value products. Further, when employing a bio-renewable raw material/feedstock which is already pre-treated (specifically a bio-renewable raw material/feedstock having the above-mentioned total contents of nitrogen, sulphur and/or phosphorus), the pretreatment step may be omitted.

14. The method according to any one of the preceding items, comprising a step of removing contaminants containing O, S, N and/or P from the propane feed.
15. The method according to item 14, wherein the step of removing contaminants from the propane feed is one or more selected from amine wash, distillation, fractionation, polishing, steam distillation, membrane separation.

Although the pre-treatment is suited to remove most of the contaminants, it may be desirable to further remove such contaminants from the propane feed in order to achieve even higher purity. On the other hand, in view of cost efficiency and in view of the already high purity which can be achieved in the pretreatment step alone, it is preferred that no purification of propane is carried out before dehydrogenation. Specifically, it is preferred that no molecular sieves, no adsorption/absorption purification and no guard bed(s) are used in/before the dehydrogenation step.

16. The method according to any one of the preceding items, wherein the propylene material has a propylene content of at least 80 wt.-%, preferably at least 85 wt.-%, at least 87 wt.-%, at least 88 wt.-%, at least 89 wt.-%, at least 90 wt.-%, at least 91 wt.-%, at least 92 wt.-%, at least 93 wt.-%, at least 94 wt.-%, at least 95 wt.-%, at least 96 wt.-%, or least 97 wt.-%.
17. The method according to any one of the preceding items, wherein the bio-renewable material in the deoxygenation step is blended with a diluent.

As explained in detail below, a diluent is particularly suited for temperature control during deoxygenation, specifically during hydrodeoxygenation.

18. The method according to item 17, wherein the diluent comprises at least one of recycled product from the deoxygenation step and a fossil-based material, preferably a hydrocarbon material.
19. The method according to item 17 or 18, wherein the blend subjected to deoxygenation contains at least 2 wt.-% of the bio-renewable raw material, preferably at least 5 wt.-%, at least 10 wt.-%, at least 20 wt.-%, at least 25 wt.-%, at least 50 wt.-%, at least 75 wt.-%, at least 85 wt.-%, at least 90 wt.-%, at least 95 wt.-%, or at least 99 wt.-%.
20. The method according to any one of items 17 to 19, wherein the blend subjected to deoxygenation contains 90 wt.-% or less, 75 wt.-% or less, or 50 wt.-% or less of the bio-renewable raw material.
21. The method according to any one of items 17 to 20, wherein the diluent comprises recycled product from the deoxygenation step and the blend subjected to deoxygenation contains at least 10 wt.-% of the recycled product from the deoxygenation step, preferably at least 25 wt.-%, at least 40 wt.-%, at least 60 wt.-%, at least 70 wt.-%, at least 80 wt.-%, or at least 85 wt.-%.

The recycled product from the deoxygenation step is preferably a hydrocarbon, but may similarly be a material which is only partially deoxygenated.

22. The method according to any one of items 17 to 20, wherein the diluent comprises recycled product from the deoxygenation step and the blend subjected to deoxygenation contains 60 wt.-% or less, 40 wt.-% or less or 25 wt.-% or less of the recycled product from the deoxygenation step.
23. The method according to any one of the preceding items, wherein the separation after the deoxygenation step to provide a propane feed comprises a step of pretreating the product from deoxygenation and then recovering the propane from the pretreated product, said pretreating step comprising removal of sour components (sweetening) from the gas stream.

24. The method according to any one of the preceding items, wherein the separation after the deoxygenation step to provide a propane feed comprises a step of separating at least propane from heavier hydrocarbon products, preferably using a distillation or evaporation technique.

25. The method according to any one of the preceding items, wherein the separation after the deoxygenation step to provide a propane feed comprises a step of separating at least propane from hydrogen, preferably using a membrane separation technique.

A specifically favorable process comprises pretreatment of the crude material coming from the deoxygenation process, separation of high-boiling components (e.g. having a higher boiling point than propane) by a distillation or evaporation technique, preferably cryogenic distillation or fractionation, and then separating the propane from hydrogen. The separation of propane from hydrogen is most preferably effected using a membrane separation technique (i.e. by use of a selective membrane) but it may also be effected by a distillation or evaporation technique, preferably cryogenic distillation or fractionation. In this case, the separation of hydrogen from propane may be carried out simultaneously (within the same process) as the separation of propane from the higher-boiling components.

A specifically preferable overall process is outlined in item 26 below:

26. The method according to any one of the preceding items, comprising the following steps:
    a) providing bio-renewable oil(s) and/or fat(s) comprising a least one of glycerol, monoglycerides, diglycerides and triglycerides, preferably at least triglycerides;
    b) pretreating the bio-renewable oil(s) and/or fat(s) to remove contaminant(s) and to provide a bio-renewable raw material, wherein the pretreatment optionally includes hydrolyzing and/or transesterifying the bio-renewable raw material, followed by separation to produce a C3 feed, preferably a glycerol feed, as the bio-renewable raw material;
    c) deoxygenating, preferably hydrotreating the bio-renewable raw material to produce a bio-hydrocarbon feed, followed by separating the propane feed from the bio-hydrocarbon feed;
    d) optionally cracking the deoxygenated C3+ stream separated from the bio-hydrocarbon feed, followed by separation of gases and combining at least propane in said gases with the propane feed;
    e) subjecting the propane feed to dehydrogenation and to separation to provide a propylene material;
    f) optionally polymerizing the propylene material or a derivative thereof to produce a polymer.

Specifically, it is preferable that the propylene or a derivative thereof is subjected to polymerization, optionally in the presence of other monomers (including macromonomers) to provide a polymer. The derivative of propylene may be any derivative commonly produced from propylene in order to provide a monomer (and/or macromonomer), such as acrylic acid, and acrylic acid ester or salt, or an alkyl (e.g. meth) acrylic acid ester/salt, butadiene or propylene oxide.

27. The method according to any one of the preceding items, comprising a step of polymerizing the propylene material or a derivative thereof, optionally in the presence of co-polymerizable monomer(s) and/or additive(s), to produce a polymer.

28. The method according to item 27, wherein the polymer is further processed to produce a sanitary article.

29. The method according to item 27, wherein the polymer is further processed to produce a construction material.

30. The method according to item 27, wherein the polymer is further processed to produce a packaging material.

31. The method according to item 27, wherein the polymer is further processed to produce a coating composition.

32. The method according to item 27, wherein the polymer is further processed to produce a paint.

33. The method according to item 27, wherein the polymer is further processed to produce a decorative material, such as a panel.

34. The method according to item 27, wherein the polymer is further processed to produce an interior part of a vehicle, such as an interior part of a car.

35. The method according to item 27, wherein the polymer is further processed to produce a rubber composition.

36. The method according to item 27, wherein the polymer is further processed to produce a tire.

37. The method according to item 27, wherein the polymer is further processed to produce a toner.

38. The method according to item 27, wherein the polymer is further processed to produce a personal health care article.

39. The method according to item 27, wherein the polymer is further processed to produce a part of a consumer good.

40. The method according to item 27, wherein the polymer is further processed to produce a part or a housing of an electronic device.

41. The method according to any one of the preceding items, comprising a step of polymerizing the propylene material, optionally in the presence of co-polymerizable monomer(s) and/or additive(s), to produce a polymer, such as polypropylene (PP), ethylene-propylene-copolymer (EPM), or ethylene-propylene-diene-copolymer (EPDM).

42. The method according to item 41, further comprising a step forming a polymer product, such as a film, a molded product, a coating composition, a coating, a packaging, a construction material, a rubber composition, a tire, a part of a tire, or a gasket, from the polymer optionally together with other components.

43. The method according to any one of items 1 to 39, comprising a step of oxidizing the propylene material to produce acrylic acid, an ester or a salt thereof, optionally further comprising a step of purifying the acrylic acid, the ester or salt thereof.

44. The method according to item 43, wherein the oxidation is carried out by gas phase oxidation.

45. The method according to item 43 or 44, comprising a step of polymerizing the acrylic acid, an ester or a salt thereof, optionally in the presence of co-polymerizable monomer(s) and/or additive(s), to produce an acrylic polymer.

In this context, acrylic acid (and acrylic polymers) are meant to include any type of acrylic-based monomers and polymers, e.g. those based on (meth)acrylic acid, (meth)acrylic acid esters, (meth)acrylic acid salts, and (meth)acrylonitriles.

46. The method according to item 45, wherein the acrylic polymer is a water-absorbing polymer.
47. The method according to item 45 or 46, wherein the polymer is further processed to produce a sanitary article.
48. The method according to item 47, wherein the sanitary article is a diaper.
49. The method according to item 47, wherein sanitary article is a sanitary napkin.
50. The method according to item 47, wherein sanitary article is an incontinence draw sheet.
51. The method according to item 45, further comprising a step of mixing the acrylic polymer with further components to produce a coating or a paint.
52. The method according to any one of items 1 to 39, comprising a step of oxidizing the propylene material to produce propylene oxide, optionally further comprising a step of purifying the propylene oxide.
53. The method according to item 52, comprising a step of polymerizing the propylene oxide, optionally in the presence of co-polymerizable monomer(s) and/or additive(s), to produce a polymer, such as a polyether, a polyether polyol, a polyester, a polyurethane, or a polymer or oligomer surfactant.
54. The method according to any one of items 1 to 39, comprising a step of converting the propylene material to produce butadiene, optionally further comprising a step of purifying the butadiene.
55. The method according to item 54, wherein the conversion step is a hydroreforming step.
56. The method according to item 54 or 55, comprising a step of polymerizing the butadiene, optionally in the presence of co-polymerizable monomer(s) and/or additive(s), to produce a polymer, such as a polybutadiene rubber (BR), an acrylonitrile-butadiene rubber (NBR, HNBR), acrylonitrile-butadiene-styrene rubber (ABS), or styrene-butadiene rubber (SBR).
57. The method according to any one of items 1 to 39, comprising a step of converting the propylene material to produce one or more selected from the group consisting of acetone, phenol, acrolein, acrylonitrile, epichlorohydrin, butanal, 1-butanol, 1,2-propandiol, 1,3-propandiol, 2-propanol, thymol.
58. A product produced by the method according to any one of items 1 to 57.

BRIEF DESCRIPTION OF THE DRAWING

Other features and advantages of the present disclosure will become more apparent upon reading the following detailed description in conjunction with the accompanying drawing, wherein:

FIG. 1 shows an exemplary embodiment wherein separation of propane from hydrogen is accomplished using a selective membrane (membrane separation) as further described in detail below.

DETAILED DESCRIPTION OF THE INVENTION

In the following, the present invention is described in detail with reference to embodiments. The invention is not necessarily limited to the embodiments. Rather, the embodiments show preferable ways how the invention can be put into practice.

Terms and expressions used in the present invention are described below.

By the term "impurities" is meant those impurities harmful or undesired in the final propylene product and/or harmful during processing thereof. These impurities usually comprise phosphorus, phosphorus compounds, nitrogen, nitrogen compounds, sulphur and compounds containing sulphur and oxygen containing compounds which are dissolved and/or miscible or chemically bound in the feed oil or fat.

By the term "pretreating the bio-renewable oil(s) and/or fat(s)" is meant a conventional process or combinations of conventional processes aiming at purification of impure oil/fat feed, i.e. removal of impurities. Preferable pretreatment comprises degumming, bleaching, heat treatment, centrifugation, filtering or any combination thereof which results in a decreased content of the impurities.

By the term "degumming" is meant a purification process wherein impure oil/fat is treated with acid, water and caustic at elevated temperature with high shear mixing. The formed gums may subsequently be separated from the oily material preferably by centrifugation and the material may be dried.

By the term "bleaching" is meant a purification process wherein acid and water is added to the impure oil/fat, and the resulting composition is mixed with an adsorbent material (such as bleaching earth) at elevated temperature and reduced pressure (such as vacuum). Thereafter the oil/fat is dried and separated from said adsorbent typically by filtration.

By the term "deodorization" is meant a purification process wherein oil is treated at an elevated temperature in reduced pressure and using steam stripping to remove impurities and/or free fatty acids.

By the term "hydrolysis of fat(s) and (oil(s)" is meant a process where an oil(s) and/or fat(s) stream predominantly containing mono-, di- and triglycerides is hydrolyzed to free up the fatty acids and glycerol by using elevated temperature and water.

By the term "heat treatment" in the context of pretreatment is meant a purification process wherein impure oil/fat is heated at elevated temperature to convert all or part of the soluble impurities into insoluble material that is subsequently removed for example by filtration or any other method.

By the term "hydrotreatment" is meant a catalytic process of organic material by all means of molecular hydrogen. Preferably, hydrotreatment removes oxygen from organic oxygen compounds as water i.e. hydrodeoxygenation (HDO), removes sulphur from organic sulphur compounds as dihydrogen sulphide (H2S), i.e. hydrodesulphurisation, (HDS), removes nitrogen from organic nitrogen compounds as ammonia (NH3), i.e. hydrodenitrofication (HDN), and removes halogens, for example chlorine from organic chloride compounds as hydrochloric acid (HCl), i.e. hydrodechlorination (HDCl).

By the term "hydrodeoxygenation" (HDO) of triglycerides or other fatty acid derivatives or fatty acids is meant the removal of carboxyl oxygen as water by the means of molecular hydrogen under the influence of catalyst.

By the term "deoxygenation" is meant removal of oxygen from organic molecules, such as fatty acid derivatives, alcohols, ketones, aldehydes or ethers by any means previously described or decarboxylation or decarbonylation.

In the following, the method of the present invention will be described in greater detail with reference to preferred embodiments for the individual process steps and raw materials, intermediate products and end products. While the invention is not limited to the preferred embodiments, it is noted that any value or condition recited in the embodiments may be combined with the general process of the present invention either individually or in combination with other preferred embodiments.

Bio-Renewable Oil(s) and/or Fat(s)

Bio-renewable oil(s) and/or fat(s) (also referred to as bio-renewable feedstock or, if pre-treated, as bio-renewable raw material) refer to a feedstock derived from a biological raw material component containing oils and/or fats, usually containing fatty acids or glycerides, such as plant oil/fats, vegetable oil/fats, animal oil/fats, fish oil/fats and algae oil/fats, or oil/fats from other microbial processes, for example genetically manipulated algae oil/fats, genetically manipulated oil/fats from other microbial processes and also genetically manipulated vegetable oil/fats. Components of such materials could also be used, such as for example alkyl esters (typically C1 C5-alkyl esters, such as methyl, ethyl, propyl, iso-propyl, butyl, sec-butyl esters). Bio-renewable specifically excludes fossil sources.

In the present invention, it is possible to employ a bio-renewable feedstock which is converted into a bio-renewable raw material by the pretreatment step. Alternatively, it is possible to employ an already pretreated bio-renewable raw material and thus the pretreatment step can be omitted. In the following, reference is made to a bio-renewable raw material (i.e. an already pretreated material), but the same applies to a (non-pretreated) bio-renewable feedstock.

The bio-renewable oils and/or fats further include a single kind of oil, a single kind of fat, mixtures of different oils, mixtures of different fats, mixtures of oil(s) and fat(s), fatty acids, glycerol and mixtures of the afore-mentioned.

These oils and/or fats typically comprise C10-C24 fatty acids and derivatives thereof, including esters of fatty acids, glycerides, i.e. glycerol esters of fatty acids. The glycerides may specifically include monoglycerides, diglycerides and triglycerides.

A typical bio-renewable raw material (or feedstock) is a glyceridic raw material (or feedstock), which is a raw material (or feedstock) that contains glycerides, i.e. one, two or three fatty acids bound to glycerol through ester linkage. The bio-renewable raw material (or feedstock) may also include glycerol. The production of propane from bio-renewable raw materials (or feedstocks) is usually based on the processing of glycerides (i.e. mono-, di-, and tri-glycerides as well as mixtures thereof). Thus, the presence of at least some glycerides within the bio-renewable raw material (or feedstock) is desirable. Raw material (or feedstock) not comprising glycerol or glycerides may also be used, such as fatty acids—here the propane is usually derived from a (hydro)cracking step. In this case, after hydrodeoxygenation the feedstock can be subjected to (hydro)cracking and/or (hydro)isomerisation such that more cracking/isomerisation reactions occur and such that these reactions results to at least some C3 material, preferably propane.

The bio-renewable raw material (or feedstock) can include at least 2 wt % of the raw material being a bio-renewable raw material (or feedstock), for example at least 5 wt %, at least 25 wt %, at least 50 wt %, at least 75 wt %, at least 90 wt % or at least 95 wt %. The raw material (or feedstock) can also be entirely a feed from a bio-renewable raw material (or feedstock) or it can include 99 wt % or less of the feed being a bio-renewable raw material (or feedstock), for example 90 wt % or less, 75 wt % or less or 50 wt % or less. With regard to the content of glycerides or glycerol, it is advantageous to have a high amount of bio-renewable raw material (or feedstock) because it usually includes a greater amount of glycerides or glycerol. Raw materials (or feedstocks) having lower amounts of bio-renewable raw material/feedstock (oils and/or fats) may have other advantages. For example, the catalytic deoxygenation of bio-renewable raw material is exothermic, which means that blending the bio-renewable raw material (or feedstock) with a portion that does not contain oxygen or a portion that is not as prone to exothermic reactions during catalytic deoxygenation conditions may be beneficial. Blending may be done for example with feedstock of mineral origin (fossil feedstock), or may be blended with a recycled product from e.g. catalytic deoxygenation of the present process having reduced oxygen content. Further, blending may be done before pretreatment, after pretreatment or both before and after pretreatement. Blending at least (preferably only) after pretreatment is favourable in view of process efficiency. If a recycled product from the catalytic deoxygenation is used for blending, it can correspond to at least 10 wt % of the feedstock being a recycled product, or it can correspond to at least 25 wt %, at least 40 wt %, at least 60 wt %, at least 70 wt %, at least 80 wt % or at least 85 wt %. The recycled product can also correspond to 60 wt % or less, such as 40 wt % or less, or 25 wt % or less.

With regards to a glyceridic or glycerol raw material (or feedstock), the raw material (or feedstock) can include at least 1 wt % glycerides or glycerol, such as at least 10 wt %, at least 20 wt %, at least 35 wt %, at least 50 wt %, at least 75 wt %, at least 90 wt %. The raw material (or feedstock) can also be composed entirely of glycerides or glycerol or the glyceride/glycerol content can be 95 wt % or less, such as 90 wt % or less, 75 wt % or less, 50 wt % or less, 40 wt % or less, 25 wt % or less. With regards to production of propane or other three carbon molecular species, a raw material (or feedstock) having higher glyceride or glycerol contents are preferred. Glyceridic raw materials (or feedstocks) preferably include triglycerides of C10-C28 fatty acids, as well as mono- and di-glyceride variants thereof.

Examples of vegetable oils usable as a bio-renewable raw material (or feedstock) or as a component thereof include, but are not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, tallow oil, and rice bran oil, or fractions of above mentioned oils such as palm olein, palm stearin, purified tall oil, and tall oil fatty acids.

Examples of animal fats usable as a bio-renewable raw material (or feedstock) or as a component thereof include, but are not limited to tallow, lard, yellow grease, brown grease, fish fat, poultry fat.

Pretreatment

A typical problem with the use of bio-renewable oil(s) and/or fat(s), such as animal based fats or vegetable oils, in particular microbial oils, for biopropylene production is that they tend to contain significant amounts of heteroatom impurities such as metals, phosphorus, sulphur, nitrogen and oxygen. The impurities cause problems, for example, in the propylene production in form of catalyst poisons. Deposits of metals, phosphorus, sulphur, nitrogen and oxygen compounds are likely to result in catalyst deactivation and plugging of the reactor catalyst bed in refining processes.

Therefore, it is required to use pretreatment steps or precleaning for removal of these undesired components from the oil product. Common treatment methods such as water degumming, soft degumming, acid degumming, wet bleaching and dry bleaching, for example, are able to remove most of the impurities (contaminants) from the feed stream.

The pretreatment step may also comprise a hydrolysis/transesterification step of glycerides and production of glycerols and fatty acids.

Deoxygenation

The gas stream may be derived from deoxygenation of a raw material containing some amount of a bio-renewable raw material as described above, such as for example a glyceridic raw material. The raw material may alternatively or additionally contain glycerol, preferably bio-renewable glycerol, which is glycerol obtained from a bio-renewable source. Bio-renewable glycerol is a by-product of the production of fatty acid esters such as for example fatty acid methyl esters (FAME), fatty acid ethyl esters (FAEE) or as a product of fat splitting. Deoxygenation preferably includes hydrodeoxygenation, which is described below under the heading Removal of oxygen from a bio-renewable raw material.

Deoxygenation, e.g. by hydrotreatment of glyceride raw material to a bio-renewable product, involves various reactions where molecular hydrogen reacts with other components, or components undergo molecular conversions in presence of molecular hydrogen and solid catalyst. The reactions include but are not limited to hydrogenation, hydrodeoxygenation, hydrodesulfurization, hydrodenitrification, hydrodemetallization, hydrocracking and isomerization.

It is preferred that the deoxygenation conditions are selected such that it provides saturated hydrocarbons.

The preparation of bio-renewable products often involves reactions removing oxygen from the bio-renewable raw material, and there are a number of strategies for doing this. The deoxygenation may comprise one or more of following reactions:

1) hydrodeoxygenation (HDO), hydrogenation of oxygen bonds—removing oxygen as H2O,
2) decarboxylation where oxygen is removed in the form of CO2, and
3) decarbonylation where oxygen is removed in the form of CO.

Preferably the deoxygenation comprises HDO. Many conditions for hydrodeoxygenation are known to the skilled person. For example the hydrodeoxygenation of a bio-renewable raw material component can be done on a metal sulphide catalyst. The metal can be one or more Group VI metals, such as Mo or W, or one or more Group VIII non-noble metals such as Co or Ni. The catalyst may be supported on any convenient support, such as alumina, silica, zirconia, titania, amorphous carbon, molecular sieves or combinations thereof. Usually the metal will be impregnated or deposited on the support as metal oxides. They will then typically be converted into their sulphides. Examples of typical catalysts for hydrodeoxygenation are molybdenum containing catalysts, NiMo, CoMo, or NiW catalysts; supported on alumina or silica, but many other hydrodeoxygenation catalysts are known in the art and have been described together with or compared to NiMo and/or CoMo catalysts. The hydrodeoxygenation is preferably carried out under the influence of sulphided NiMo or sulphided CoMo catalysts in the presence of hydrogen gas.

The hydrodeoxygenation is preferably performed under a hydrogen pressure from 10 to 200 barg (bar gauge), at temperatures from 200 to 400° C., and liquid hourly space velocities of 0.2 h$^{-1}$ to 10 h$^{-1}$. During the hydrodeoxygenation step using a sulfided catalyst, the sulfided state of the catalyst is preferably maintained by addition of sulphur (or a sulphur compound) in the gas phase or by using a material having a sulphur containing mineral oil blended with the bio-renewable raw material. The sulphur content of the total feed being subjected to hydrodeoxygenation is preferably 50 wppm (ppm by weight) to 20000 wppm, more preferably in the range of 100 wppm to 1000 wppm.

Effective conditions for hydrodeoxygenation preferably reduce the oxygen content of the raw material to less than 1 wt %, such as less than 0.5 wt % or less than 0.2 wt %. In some cases, the conditions may be selected to yield partial hydrodeoxygenation corresponding to a deoxygenation of at least 40 wt %, at least 50 wt % or at least 75 wt %.

The hydrodeoxygenated product (crude material) may be separated into a gas stream and a liquid stream. The gas stream comprises hydrogen that has not been used as well as propane. When the bio-renewable raw material contains triglycerides, propane is obtained mainly from hydrogenation of the glycerol moiety, and to a lesser extent from cracking of the fatty acids.

In various embodiments the gas stream may further comprise at least one further gas chosen from the group consisting of: $H_2O$, $CO_2$, CO, $H_2S$, $NH_3$, $PH_3$ and light hydrocarbons. Carbon oxides (CO and $CO_2$) are often present in gas streams from processing of bio-renewable raw material.

Separation of Propane Feed

After performing hydrodeoxygenation under effective conditions, as described above, propane will be present as one of a variety of gas phase components. The deoxygenation product is preferably separated into a gas stream and a liquid stream as a first separation step. Besides the hydrogen that has not been used as well as the generated propane, the gas stream may also include, but is not limited to, other hydrodeoxygenation reaction products, such as $H_2S$, as well as $H_2O$, $CO_2$ and CO from the hydrogenation, decarboxylation and decarbonylation reactions, although the amounts will not necessarily represent the extent of these reaction types because of the water-gas shift reaction where CO and $H_2O$ are in equilibrium with $CO_2$ and $H_2$. Additionally there may be light hydrocarbons, for example as a result of cracking, in addition to propane.

The light hydrocarbons include the gaseous light hydrocarbons, i.e. hydrocarbons that are in the gas phase at the pressure and temperature of the gas stream that is to be treated according to the present invention. The light hydrocarbons may for example be hydrocarbons having fewer than seven carbon atoms, i.e. C1-C6 hydrocarbons, which include, but is not limited to: methane, ethane, propane, butane, 2-methylpropane, pentane, isopentane, neopentane, hexane, 2-methylpentane, 3-methylpentane, 2,3-dimethylbutane, 2,2-dimethylbutane. The light hydrocarbons may further be distinguished into light hydrocarbons having a carbon number of 4 or less and light hydrocarbons having a carbon number of 5 or more, e.g. light hydrocarbons having a carbon number of 5-10 or 5-8. In addition to light hydrocarbons, there could also be hydrocarbons having seven or more carbon atoms, for example C7-C10 hydrocarbons, but they would normally only be present in a few tens of ppm.

Hydrogen is usually present in the gas stream as a major component. The gas stream may contain at least 70 mol-% hydrogen, such as at least 75 mol % hydrogen, at least 80 mol-% hydrogen. The hydrogen content may be less than 95 mol-%, such as less than 90 mol-%.

Propane is also present in the gas stream and the amount depends mainly on the content of triglycerides in the raw material and to a lesser extent on cracking. The gas stream may contain at least 1 mol-% propane, such as at least 3 mol % propane. The gas stream may also contain 25 mol-% or less propane, such as 20 mol-% or less, or 15 mol-% or less. When the gas stream is derived from a bio-renewable raw material the content of the gas stream is often 25 mol-% or less.

In various embodiments the temperature of the gas stream is between 5° C. and 95° C., and the pressure is between 20 barg and 60 barg.

Pretreatment of the Gas Stream Obtained after Deoxygenation

Depending on the composition of the gas stream, it may undergo one or more pretreatment steps before it is separated from hydrogen, e.g. by being passed across the feed side of the membrane.

In particular if the gas stream is sour, meaning that it contains $H_2S$, $CO_2$ or both $H_2S$ and $CO_2$, it can undergo sweetening to remove excess $H_2S$ and $CO_2$. The sour gas may be harmful to the membrane material, in particular the presence of $H_2S$. The gas stream is considered to be sour, if it contains 5 wppm or more $H_2S$, such as 25 wppm or more, 50 wppm or more, 75 wppm or more, 100 wppm or more, 150 wppm or more, or 200 wppm or more. Sweetening of the gas should preferably reduce the $H_2S$ content to 1 wppm or lower, such as 0.5 wppm or lower, or 0.1 wppm or lower.

The gas stream is considered to be sour, if it contains 3000 wppm or more $CO_2$, such as 4000 wppm or more, 5000 wppm or more, 7500 wppm or more, 10000 wppm or more, 20000 wppm or more or 50000 wppm or more. Sweetening of the gas should preferably reduce the $CO_2$ content to 3000 wppm or lower, such as 2000 wppm or lower, or 1000 wppm or lower, or 500 wppm or lower, or 100 wppm or lower, or 10 wppm or lower, such as 1 wppm or lower, and $H_2S$ content to 50 wppm or lower, 10 wppm or lower, 5 wppm or lower, or such as 1 wppm or lower.

The gas may be sweetened using an amine scrubber, or other unit processes used in e.g. refineries, at conditions that reduce or remove both the $H_2S$ and the $CO_2$.

Accordingly, when the gas stream is sour and at least further comprises $CO_2$ and/or $H_2S$, the gas stream may be subjected to a sweetening step, such as an amine scrubbing step, to remove at least a portion of the $CO_2$ and/or $H_2S$ gas components before being provided to the membrane. The amine scrubbing step sweetens the sour gas stream.

Separation of Propane and Hydrogen from the Gas Stream

In order to recover propane from the gas stream, the deoxygenated product is preferably first separated into the gas stream and a liquid stream, as explained above. The liquid stream will typically contain hydrocarbons in the diesel boiling range, and is thus suitable for the production of renewable diesel. The propane and hydrogen from the gas stream comprising hydrogen and propane can then be separated from the remaining gas stream.

In the method for treating the gas stream, treating the gas stream may be separating both propane and hydrogen from the remaining gas stream and then separating propane from hydrogen.

An exemplary embodiment of the present invention is shown in FIG. 1, wherein separation of propane from hydrogen is preferably accomplished using a selective membrane (membrane separation) and this embodiment is described in detail below. However, the invention is not limited to this embodiment and other methods for separating propane from hydrogen (and optional at the same time from other gaseous components) may be accomplished using any other suitable method, such as cryogenic distillation or swing adsorption.

Step a)

The method of separating propane from hydrogen according to an embodiment of the invention involves a step of providing a membrane. The membrane has a feed side and a permeate side. The membrane works by being selective for hydrogen over propane, in that it preferentially permeates most of hydrogen and rejects most of propane. If present, the one or more of the further gasses chosen from the group consisting of: CO and light hydrocarbons are also rejected together with propane, while $H_2O$, $CO_2$, $H_2S$ and $NH_3$ would be rejected or only partially rejected depending on the membrane type and conditions, e.g. temperature and pressure.

Step b)

In its most basic aspect, the membrane separation involves passing the gas stream containing these components across the feed side of the membrane that is hydrogen selective. A driving force for transmembrane permeation is provided by a higher pressure on the feed side than on the permeate side. For example the pressure on the feed side can include a pressure of 10 barg or higher, such as 20 barg or higher, or 30 barg or higher, or 40 barg or higher, or 50 barg or higher and the pressure on the permeate side can include a pressure that is at least 1 bar lower than the feed side, such as 5 bar or lower, or 10 bar or lower, or 20 bar or lower, or 30 bar or lower. The membrane can be made from polymeric, ceramic or metal materials well known in the art of membrane science, such as cellulose acetate, polysulfone, polyimide, polyamide, zeolite, or palladium, and can be in form of spiral wound membrane, hollow fiber membrane, tube or plate.

Step c)

After membrane separation stage, a retentate stream depleted in hydrogen and enriched in propane compared to the crude gas stream can be withdrawn from the feed side.

The retentate stream may contain less than 65 mol-% hydrogen, such as less than 55 mol %, less than 40 mol-%, less than 25 mol-%. The retentate stream may also contain more than 5 mol-% hydrogen, such as more than 10 mol-% hydrogen. The membrane is usually operated such that there will remain some hydrogen in the retentate stream because it will result in a higher purity of hydrogen in the permeate stream.

The retentate stream may also contain more than 15 mol-% propane, for example more than 25 mol-% propane, more than 30 mol-% propane. The retentate stream may also contain less than 75 mol-% propane, such as less than 65 mol-% propane, or less than 55 mol-% propane.

Step d)

After membrane separation stage, a permeate stream enriched in hydrogen and depleted in propane compared to the crude gas stream can be withdrawn from the permeate side.

In various embodiments, the membrane stage cut, defined as the fraction of the gas stream that permeates the membrane, may correspond to at least 10%, such as at least 15%, or at least 20%, at least 25%, at least 30%, at least 40%, at least 50%, or at least 75%. The stage cut can also correspond to 95% or less, such as 80% or less, 70% or less, 50% or less. The higher the stage cut, the less pure the hydrogen in the permeate will be. The permeate stream may be used as a recycle hydrogen gas.

Pre-Treatment of the Retentate Stream

The retentate stream may still comprise further gas species in addition to propane and hydrogen, which include, but is not limited to $H_2O$, $CO_2$, $H_2S$, CO and other gaseous light hydrocarbons in addition to propane. If the gas is sweet, the further gas species will include, but is not limited to $H_2O$, CO and other gaseous light hydrocarbons in addition to propane.

The retentate stream may be subjected to one or more supplementary treatment steps to remove at least a portion of the further gas species described above before being subjected to further separation e.g. using elevated pressure distillation.

The one or more supplementary treatment steps include, but are not limited to: removal of water through e.g. gas drying by adsorption water vapour on a surface, or by absorption on e.g. a dehydrating agent such as glycol or a solid desiccant. Low temperature separation may also be employed to remove water or part of it, as well as some light hydrocarbons, at temperatures below 60° C., such as 50° C. or lower, 40° C. or lower, 30° C. or lower but preferably at temperatures above 5° C.

Step e)

The retentate stream being depleted in hydrogen and enriched in propane compared to the crude gas stream may be subjected to fractionation by distillation, such as cryogenic separation and/or elevated pressure distillation in order to separate hydrogen from propane. The retentate stream being subjected to the fractionation is preferably depleted in hydrogen and enriched in propane compared to the gas stream coming from the membrane separation stage, and further preferably depleted or being essentially free of $NH_3$, $H_2O$, $CO_2$, $PH_3$ and $H_2S$ and light hydrocarbons. Additionally, the retentate stream being depleted in hydrogen and enriched in propane compared to the gas stream coming from the membrane separation stage may also comprise further gas species, which includes, but is not limited to CO and $CO_2$ and other gaseous light hydrocarbons in addition to propane.

An elevated pressure distillation may be conducted in a pressurised distillation column, where there is a vertical temperature gradient. In various embodiments the elevated pressure distillation could be considered cryogenic separation, in that the elevated pressure distillation may be conducted at temperatures above −100° C., such as above −85° C., above −70° C., such as above 0° C. The temperature range for the distillation column is preferably from −70° C. to 130° C. The bottom of the pressurised distillation column (measured at the valve from which of the column's bottom product is withdrawn) may have a temperature of 80° C. to 130° C.

The elevated pressure distillation is preferably conducted so as to ensure sufficient theoretical plates so that hydrogen and other light hydrocarbons such as C1 and C2 as well as CO, $CO_2$ can be separated from propane. In the lower section of the column, the propane is separated from the C4 and C5. These may be purged with a small portion of the propane, back to the diesel stabilisation section of the renewable diesel plant. If further gas species are present, which include, but are not limited to CO and $CO_2$ and other gaseous light hydrocarbons in addition to propane, it is advantageous that conditions are provided to ensure sufficient theoretical plates to separate propane from the further gas species.

The elevated pressure distillation may be conducted at pressures above 20 barg, such as between 25 and 40 barg. The elevated pressure distillation may be performed between −70° C. and 130° C. at such pressures. For example between 0° C. and 130° C.

Apart from being dehydrogenated in the process of the present invention, the propane obtained from the elevated pressure distillation may be formulated into a propane-containing product. The propane-containing product may comprise the addition of an odorizing agent, such as for example comprising an odorizing agent selected from one or more of: tert-butylthiol, tetrahydrothiophene and ethanethiol. This product may further be transported to a consumer that could consume the product for example for heating, a fuel for a vehicle, or cooking.

In the present invention, the propane obtained from the elevated pressure distillation will with or without further formulation preferably have a minimum content of 95% (wt/w) propane and/or have a maximum of 5% propylene, the remainder being and light hydrocarbons, such as isobutane, butane, ethane, methane, constituting the remainder. For example the propane obtained may with or without further formulation fulfil one or more of EN 589, DIN 51622, BS 4250 or HD 5 propane specifications. In some embodiments, the propane obtained from the elevated pressure distillation does not contain propylene because it is derived from a source that does not contain propylene to start out with, e.g. if conditions for deoxygenation has been sufficiently severe to ensure that all existing olefins have been hydrogenated and no olefins are formed.

According to the present invention, the propane product is dehydrogenated to propylene.

The hydrogen obtained from the elevated pressure distillation may be combined with the permeate stream and at least partly recycled. Alternatively, part of the hydrogen obtained from the elevated pressure distillation may be combined with the permeate stream.

Membrane

The membrane employed in the preferred membrane separation process is hydrogen selective, in that it selectively permeates hydrogen. Various hydrogen permeable membranes are known in the art, and some of the membranes are based on polymeric, ceramic or metal materials well known in the art of membrane science, such as polysulfone, polyimide, polyamide, cellulose acetate, zeolite or palladium. The membrane may have any suitable shapes and sizes, such as for example it may be in the form of a spiral wound membrane, hollow fibre membrane, tube membrane or plate membrane. The actual selectivity for hydrogen over propane depends on the material that the membrane is made out of, as well as the process conditions, including the temperature and the pressure on the feed side and the permeate side, respectively.

The membrane material and conditions for membrane separation is preferably chosen so that the membrane being selective for hydrogen over propane exhibits a selectivity for hydrogen over propane of at least 5, such as at least 10, at least 20, at least 30, at least 50, or at least 60, measured as pure component permeability ratio (vol/vol).

In some embodiments a membrane is provided having a feed side and a permeate side, the membrane being selective for hydrogen over propane. A crude gas stream comprising between 75 and 90 mol % hydrogen and between 5 and 10 mol % propane is being passed across the feed side of the membrane resulting in a retentate gas stream and a permeate gas stream. The retentate gas stream being depleted in hydrogen (between 40 and 60 mol %) and enriched in propane (between 30 and 50 mol %). The permeate gas stream being hydrogen enriched (more than 96 mol %) and depleted in propane (less than 0.5 mol %). Subjecting then the retentate stream to elevated pressure distillation to further separate hydrogen from pressure yields a combined hydrogen recovery of more than 85 mol %.

Dehydrogenation of Propane

In the dehydrogenation process, propane gas is contacted with a catalyst. The contacting maybe accomplished in a fixed catalyst bed system, a moving catalyst bed system, a fluidized bed system, or a in a batch-type operation. The dehydrogenation reactor may comprise one or more separate reactor zones with heating. The propane gas may be contacted with the catalyst composite in either upward, downward or radial flow fashion. The propane maybe be in the liquid phase, a mixed vapor-liquid phase or the vapor phase in contacts the catalyst. Preferably, the propane is in the vapor phase.

Dehydrogenation conditions preferably include a temperature of from 150° C. to 820° C., a pressure of from 0.1 to 2530 kPa (absolute) and a liquid hourly space velocity of about 0.01 to about 50 $hr^{-1}$.

The dehydrogenation is more preferably carried out at a temperature of from 540° C. to 650° C., even more preferably from 560° C. to 630° C.

In addition, the dehydrogenation is more preferably carried out at a pressure of from 0.4 to 500 kPa (absolute), even more preferably from 0.5 to 400 kPa.

In addition, the dehydrogenation is more preferably carried out at a liquid hourly space velocity of about 1 to about 30 $hr^{-1}$, even more preferably about 5 to about 25 $hr^{-1}$.

Accordingly, the most preferred conditions are a temperature of from 560° C. to 630° C., a pressure of from 0.5 to 400 kPa and a liquid hourly space velocity of about 5 to about 25 $hr^{-1}$.

The dehydrogenation catalyst composite should exhibit high activity, high selectivity and good stability. Preferred catalytic composites comprises group VIII noble metals and a solid inorganic carrier. Such catalytic composites are well known to those skilled in the art. Particularly preferred catalyst composites include the platinum on alumina catalysts and chrome on alumina catalysts.

Dehydrogenation Products

The term "dehydrogenation products" may refer to products obtained directly after a dehydrogenation step, or to derivatives thereof, i.e. "dehydrogenation products" as used herein refers to propylene and its derivatives. "Obtained directly after a catalytic dehydrogenation step" may be interpreted as including optional separation and/or purification steps. As used herein, the term "dehydrogenation product" may also refer to the mixture of hydrocarbons obtained directly after the dehydrogenation step as such.

The propylene obtained or obtainable with the method according to the invention is particularly suitable as raw materials for conventional petrochemistry, and polymer industry. Thus, the propylene can be added to the known value-added chain while no significant modifications of production processes are required.

The propylene may be further modified to give derivatives of propylene. Propylene derivatives, which may be produced in accordance with the present invention, include, among others, isopropanol, acrylonitrile, polypropylene, propylene oxide, acrylic acid, allyl chloride, oxoalcohols, cumens, acetone, acrolein, hydroquinone, isopropylphenols, 4-hethylpentene-1, alkylates, butyraldehyde, ethylene-propylene elastomers, and their derivatives. Propylene oxide derivatives include, for example, propylene carbonates, allyl alcohols, isopropanolamines, propylene glycols, glycol ethers, polyether polyols, polyoxypropyleneamines, 1,4-butanediol, and their derivatives. Allyl chloride derivatives include, for example, epichlorohydrin and epoxy resins. Isopropanol derivatives include, for example, acetone, isopropyl acetate, isophorone, methyl methacrylate, polymethyl methacrylate, and their derivatives. Butyraldehyde derivatives include, for example, acrylic acid, acrylic acid esters, isobutanol, isobutylacetate, n-butanol, n-butylacetate, ethylhexanol, and their derivatives. Acrylic acid derivatives include, for example, acrylate esters, polyacrylates and water absorbing polymers, such as super absorbents, and their derivatives.

The propylene or the propylene derivative(s) may further be subjected to additional processes, such as polymerization, to provide subsequent products (propylene products), such as polymers.

The propylene product of the current invention may be used in a wide variety of applications. Such applications are, for example, consumer electronics, composites, automotive, packaging, medical equipment, agrochemicals, coolants, footwear, paper, coatings, adhesives, inks, pharmaceuticals, electric and electronic appliances, sport equipment, disposables, paints, textiles, super absorbents, building and construction, fuels, detergents, furniture, sportswear, solvents, plasticizers, high octane gasoline, synthetic rubber and perfumes.

EXAMPLES

Animal fat (AF) originating from food industry waste and crude palm oil (CPO) were blended to give a mixture of 50 wt-% AF and 50 wt-% CPO. This bio-renewable oil/fat raw material was first pre-treated to remove elemental impurities by bleaching. After this the pre-treated raw material stream was processed through hydrodeoxygenation (HDO) to produce a bio-hydrocarbon feed under the conditions specified below. The bio-hydrocarbon stream was separated and purified to provide a propane feed. Table 1 shows the heteroatom impurities in the bio-renewable oil/fat raw material prior the pre-treatment.

Bleaching

The bio-renewable oil/fat raw material was bleached by adding to the heated raw material 2000 ppm citric acid, 0.2 wt-% water and 1 wt % bleaching earth. These were mixed for 20 min at 80° C. after which the material was dried using reduced pressure and filtered.

Hydrodeoxygenation

The pretreated raw material was then hydrodeoxygenated in the presence of hydrogen and catalyst. The reaction temperature was 305° C., reactor pressure was 5 MPa and space velocity was 0.5 g/g. The HDO treatment resulted in a propane rich gas stream.

Separation and Purification of Propane Feed

The propane rich gas stream was first subjected to amine wash; amine flow vs. gas flow, 5.8 t/hr amine solution per ton sour gas, aqueous amine solution is 50 wt % methyl diethyl amine (MDEA), containing 400 ppm piperazine to enhance $CO_2$ absorption in an absorber at 4 MPa, (gas inlet temperature: 40° C., amine inlet temperature: 55° C.). The sweet gas was then passed across a hydrogen selective membrane. The propane rich retentate was then dried to remove water before the propane product was separated in an elevated pressure distillator at 30 barg and 50° C. to provide a propane feed. Heteroatom impurities N (ASTM D4629), P (ASTM D5185), S (ASTMD6667M) and O (ASTM D7423) were analyzed from the propane product (Table 1). The amount of heteroatom impurities N, P, S and O were below 10 ppm.

TABLE 1

Propane and heteroatom content in the raw material and the propane product

|  |  | Crude fat and oil raw material | Propane feed |
|---|---|---|---|
| Propane | wt-% | n.a. | 96.19 |
| N | mg/kg | 139.6 | <2 |
| P | mg/kg | 25.3 | <1 |
| S | mg/kg | 31.1 | 2 |
| O | mg/kg | n.a. | <10 |

The propane feed was found to cause exceptionally low catalyst poisoning when being subjected to dehydrogenation.

The invention claimed is:

1. A method for producing propylene, the method comprising:
   pretreating bio-renewable oil(s) and/or fat(s) to provide a bio-renewable raw material;
   deoxygenating the bio-renewable raw material, followed by separation, to provide a feedstock including a propane feed; and
   subjecting the propane feed to catalytic dehydrogenation and to separation to provide a propylene material,
   wherein the bio-renewable oil(s) and/or fat(s) comprise at least one or more of glycerol, monoglycerides, diglycerides and/or triglycerides,
   wherein the pretreating is a reducing of contaminants containing S, N and/or P in the bio-renewable oil(s) and/or fat(s) to produce the bio-renewable raw material, and
   wherein the propane feed has a propane content of at least 80 wt.-%.

2. The method according to claim 1, wherein the deoxygenation is at least one process selected from a group consisting of hydrodeoxygenation, decarboxylation, decarbonylation, and hydrocracking.

3. The method according to claim 1, comprising:
   subjecting C3+ components produced in the deoxygenation and separated from the propane feed to cracking to produce additional gases, followed by separation of at least propane in the additional gases and combining the separated propane with the propane feed.

4. The method according to claim 1, comprising:
   isomerizing the feedstock after the deoxygenation.

5. The method according to claim 1, wherein the pretreating comprises:
   one or more pretreating processes selected from washing, degumming, bleaching, distillation, fractionation, rendering, heat treatment, evaporation, filtering, adsorption, hydrodeoxygenation, centrifugation and/or precipitation.

6. The method according to claim 1, wherein the pretreating of the bio-renewable raw material comprises:
   at least one or more of partial hydrogenation, partial deoxygenation, hydrolysis and transesterification.

7. The method according to claim 1, wherein the bio-renewable raw material comprises glycerol and/or fatty acid esters.

8. The method according to claim 1, wherein the bio-renewable raw material contains a total sulfur content of at most 500 ppm; and/or
   wherein the bio-renewable raw material has a total phosphorus content of at most 300 ppm; and/or
   wherein the bio-renewable raw material has a total nitrogen content of at most 400 ppm.

9. The method according to claim 1 comprising:
   removing contaminants containing O, S, N and/or P from the propane feed, by one or more processes selected from amine wash, distillation, fractionation, polishing, steam distillation, and/or membrane separation.

10. The method according to claim 1, wherein the propylene material has a propylene content of at least 80 wt.-%.

11. The method according to claim 1, comprising:
    blending the bio-renewable raw material in the deoxygenation step with a diluent, wherein the blend subjected to deoxygenation contains at least 2 wt.-% of the bio-renewable raw material.

12. The method according to claim 11, wherein the diluent contains recycled product from the deoxygenation, and the blend subjected to deoxygenation contains at least 10 wt.-% of the recycled product from the deoxygenation.

13. The method according to claim 1, wherein the separation after the deoxygenation to provide a propane feed comprises:
    separating at least propane from hydrogen using a membrane separation technique.

14. The method according to claim 1, comprising:
    a) providing bio-renewable oil(s) and/or fat(s) containing at least one of glycerol, monoglycerides, diglycerides and/or triglycerides;
    b) pretreating the bio-renewable oil(s) and/or fat(s) to remove contaminant(s) and to provide a bio-renewable raw material; wherein
       the pretreating optionally includes hydrolyzing and/or transesterifying the bio-renewable raw material, followed by separation to produce a C3 feed as the bio-renewable raw material;
    c) deoxygenating, by hydrotreating, the bio-renewable raw material to produce a bio-hydrocarbon feed, followed by separating the propane feed from the bio-hydrocarbon feed;
    d) optionally cracking a deoxygenated C3+ stream separated from the bio-hydrocarbon feed, followed by separation of gases and combining at least propane in said gases with the propane feed;
    e) subjecting the propane feed to dehydrogenation and to separation to provide a propylene material; and
    f) optionally polymerizing the propylene material or a derivative thereof to produce a polymer.

15. The method according to claim 1, comprising:
    polymerizing the propylene material or a derivative thereof, in a presence of co-polymerizable monomer(s) and/or additive(s), to produce a polymer.

16. The method according to claim 15, comprising:
    forming a polymer product, and/or a film, a molded product, a coating composition, a coating, a packaging, a construction material, a rubber composition, a tire, a part of a tire, or a gasket, from the polymer optionally together with other components.

17. The method according to claim 1, comprising:
    separating a deoxygenation product obtained by deoxygenating the bio-renewable raw material into a gas stream and a liquid stream; and thereafter
    separating both propane and hydrogen from a remaining gas stream and then separating propane from hydrogen.

18. The method according to claim 1, wherein:
    the feedstock further includes a purified recycle hydrogen gas stream, and
    the deoxygenating comprises hydrodeoxygenating by using the recycle hydrogen gas stream.

19. The method according to claim 1, wherein the biorenewable oil(s) and/or fat(s) comprise at least 50 wt % of the one or more of glycerol, monoglycerides, diglycerides or triglycerides.

20. The method according to claim 1, wherein the biorenewable oil(s) and/or fat(s) comprise at least 75 wt % of the one or more of glycerol, monoglycerides, diglycerides or triglycerides.

21. The method according to claim 1, wherein the biorenewable oil(s) and/or fat(s) further comprise fatty acids.

22. The method according to claim 1, further comprising:
   subjecting the propane feed, prior to the catalytic dehydrogenation, to one or more selected from amine wash, distillation, fractionation, polishing, steam distillation, or membrane separation.

\* \* \* \* \*